United States Patent [19]

Illum

[11] Patent Number: 5,725,871
[45] Date of Patent: Mar. 10, 1998

[54] DRUG DELIVERY COMPOSITIONS COMPRISING LYSOPHOSPHOGLYCEROLIPID

[75] Inventor: Lisbeth Illum, Nottingham, United Kingdom

[73] Assignee: Danbiosyst UK Limited, Nottingham, United Kingdom

[21] Appl. No.: 260,611

[22] Filed: Jun. 15, 1994

Related U.S. Application Data

[63] Continuation of Ser. No. 834,296, filed as PCT/GB90/01293, Aug. 16, 1990, abandoned.

[30] Foreign Application Priority Data

Aug. 18, 1989 [GB] United Kingdom ............ 8918879

[51] Int. Cl.$^6$ ............... A61K 9/08; A61K 9/16; A61K 38/00
[52] U.S. Cl. ............ 424/434; 424/489; 424/499; 514/78; 514/21; 514/2; 514/866; 514/964
[58] Field of Search ................. 424/434, 435, 424/489; 514/78, 866, 964, 965, 2-4, 21; 554/79

[56] References Cited

U.S. PATENT DOCUMENTS 5,049,389  9/1991  Radhakrishnan ............... 424/434

FOREIGN PATENT DOCUMENTS

| 0162239 | 11/1985 | European Pat. Off. . |
| 2107985 | 5/1985 | United Kingdom . |
| 8809163 | 12/1988 | United Kingdom . |
| 8809163 | 1/1988 | WIPO . |
| 8804556 | 6/1988 | WIPO . |

OTHER PUBLICATIONS

Moloney. Arch. Dermathor. Res. 280, 67–70 (1988).
Epand BBRC. 152 #1, p. 203, 1988.

Primary Examiner—Gollamudi S. Kishore
Attorney, Agent, or Firm—Arnall Golden & Gregory, LLP

[57] ABSTRACT

Compositions for trans-mucosal delivery, e.g. intranasal, include a lysophosphatidyl-glycerol compound as the adsorption enhancer. The preferred compounds for delivery are insulin and calcitonin.

10 Claims, 12 Drawing Sheets

DRUG DELIVERY COMPOSITIONS COMPRISING LYSOPHOSPHOGLYCEROLIPID

This is a continuation of application Ser. No. 07/834,296 filed Feb. 18, 1992 now abandoned, International Application PCT/GB90/01293 filed on Aug. 16, 1990 and which designated the U.S.

BACKGROUND OF THE INVENTION

The present invention relates to drug delivery compositions and more particularly to a composition which provides for the uptake of active drug material across mucosal surfaces, such as the vagina or the nasal cavity.

A major problem in drug delivery is the effective absorption of high molecular weight material such as proteins and peptides across biological membranes. Normally such molecules are not taken up by the body if administered to the gastrointestinal tract, to the buccal mucosa, to the rectal mucosa, the vaginal mucosa or given as an intranasal system. Recent studies with the material insulin have demonstrated that the absorption of such a compound can be increased if it is given together with a so-called absorption enhancer. These absorption enhancing materials have included surfactants of the non-ionic type as well as various bile salt derivatives. An increased permeability of membranes in the presence of these types of surfactant material is not unexpected, indeed the literature in the field of gastroenterology contains a wide range of such absorption promoters. (For a review see Davis et al (editors), Delivery Systems for Peptide Drugs, Plenum Press, New York, 1987). However, such materials will probably not be acceptable for the chronic administration of pharmacological agents because of their irritant effects on membranes. This includes not only the non-ionic variety of surface active agents but also bile salts and bile salt derivatives (e.g. fusidic acid).

A microsphere preparation for nasal delivery has been described in PCT/GB86/00721 (Fisons). This refers only to one specific drug (sodium cromoglycate) for local effect rather than delivery to the general circulation. (See also J. Controlled Release, 1, 15–22, 1984). Most importantly, the function of the ion exchange materials was to keep the drug in contact with the mucosal surface for longer periods, not to enhance absorption.

Similarly, Miromoto and colleagues (J. Pharm. Pharmacol. vol 37 pages 135–136 1985) have used a nasal gel (once again polyacrylic acid) as a delivery system for insulin and calcitonin in rats. A significant decrease in plasma glucose levels was obtained as compared to the normal formulation, indicating an increase in the absorption efficiency.

At the present time the nose is being proposed as an alternative route for the delivery of drugs that will act within the systemic circulation. Particular attention is being focused on nature-identical peptides or proteins, or analogues or fragments thereof, produced by recombinant DNA techniques. Other drugs that are being suggested are those that are poorly absorbed orally or are extensively metabolised either in the gastroin-testinal tract itself or are subject to first pass metabolism in the liver.

However, most polypeptide drugs show a low bio-availability when administered intranasally.

The rapid clearance of nasal sprays from the nose can probably be considered to be a major factor in influencing loss of drugs from potential absorption surfaces. In addition, in the case of peptides and proteins, enzymatic degradation of the drug and molecular size may also have a role in giving low bio-availabilities.

Our earlier co-pending application WO 88/09163 discloses intra-nasal microsphere formulations containing an enhancer, such as lysophosphatidylcholine. WO 88/04556 also discloses enhancers for use in intranasal drug formulations, preferred enhancers being phosphatidylcholines and phosphatidylethanolamines. Phosphatidyl and lysophosphatidyl derivatives of glycerol are claimed, in a broad group of possible enhancers, but there are no specific examples, lysophosphatidylglycerol is not specifically mentioned and the disclosure only relates to compounds wherein the fatty acid moieties have up to 14 carbon atoms each.

It has been shown (Vrije et al Nature Vol. 334 14 July 1988) that phosphatidylglycerol is involved in the translocation of newly synthesized outer membrane proteins across the inner membrane in mutants of *E. coli* defective in the synthesis of the major anionic membrane phospholipids. However it is not yet known whether the involvement of phosphatidylglycerol in the protein translocation pathway across the *E. coli* inner membrane is in a direct or indirect manner. There is no suggestion that phosphatidylglycerol may be effective at membranes other than *E. coli* or that substances other than *E. coli* outer membrane proteins are affected.

SUMMARY OF THE INVENTION

It has now been found that lysophosphatidylglycerol compounds greatly promote the absorption of pharmacologically active compounds in microsphere formulations across the nasal mucosa.

DETAILED DESCRIPTION OF THE INVENTION

The invention therefore provides a drug delivery system comprising a pharmacologically active compound and an absorption enhancer wherein the absorption enhancer is a phosphoglycerolipid of the general formula I.

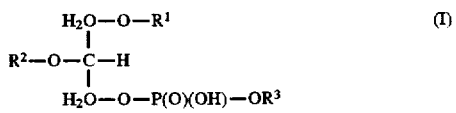

wherein one of $R^1$ and $R^2$ is hydrogen and the other is selected from the group consisting of alkyl, alkenyl, alkylcarbonyl, alkenylcarbonyl, alkadienylcarbonyl, alkatrienylcarbonyl and alkatetraenylcarbonyl groups and $R^3$ is 2,3-dihydroxy-propyl, or a physiologically acceptable salt thereof.

By alkyl, alkenyl, alkadienyl, alkatrienyl and alkatetraenyl, we mean $C_{1-30}$ alkyl, $C_{2-30}$ alkenyl, $C_{3-30}$-alkadienyl, $C_{4-30}$ alkatrienyl and $C_{5-30}$ alkatetraenyl, respectively.

Preferably, the non-hydrogen one of $R^1$ and $R^2$ is alkylcarbonyl or alkenylcarbonyl, preferably alkylcarbonyl. Advantageously the alkylcarbonyl or alkenylcarbonyl moiety contains between 14 and 18 carbon atoms and conveniently contains more than 14 carbon atoms. Examples include oleyl, palmitoyl, stearyl and myristoyl. The compound is preferably lysophosphatidylglycerol containing mainly palmitic and stearic acids (for example the product available from Sigma as L1756).

The terms "pharmacologically active agent" and "drug" are used interchangeably to embrace small molecules, hormones, polypeptides and vaccines or components thereof, for example isolated antigens or antigenic parts or mimics thereof.

The compositions of the invention may be made up as solutions or may incorporate microspheres. Preferably the microspheres are administered in the form of a freeze-dried powder by spraying and have bio-adhesive properties. The microspheres should be of a size between 10 and 100 microns, preferably 40–60 μm, (after swelling) and prepared from a biocompatible material that will gel in contact with the mucosal surface. Substantially uniform, solid microspheres are preferred. Starch microspheres (cross-linked if necessary) are a preferred material and are commercially available (e.g. as "Spherex", from Pharmacia, Uppsala, Sweden). Other microspheres include dextran, dextran derivatives, gelatin, albumin and collagen. Preparation of these microsphere systems is well described in the pharmaceutical literature (see for example Davis et (Eds), "Microspheres and Drug Therapy", Elsevier Biomedical Press, 1984, which is incorporated herein by reference). Emulsion and phase separation methods are both suitable. The final microspheres can be modified by chemical crosslinking or heat treatment. The active agent can be incorporated into the microspheres during their formulation or sorbed into/onto the system after preparation. The effectiveness of the system can be controlled by the physical nature of the microsphere matrix and, for example, the extent of the crosslinking. The microsphere delivery systems may also include microspheres made from the active peptide or protein itself such as insulin microspheres.

As an added advantage the particles may have variable controlled release characteristics through modifications made to the microsphere system, for example by controlling the degree of cross-linking or by the incorporation of excipients that alter the diffusional properties of the administered drug. The amount of drug that can be carried by the microspheres is termed the loading capacity, which is determined by the physico-chemical properties of the drug molecule and in particular its size and affinity for the particle matrix.

Other enhancers may be included, as well as the compounds of the invention, if desired. If another enhancer is present, it is preferably microspheres of starch. Use of other known enhancers, such as mucolytic agents or inhibitors of nasal proteases, is generally not preferred because of the toxic effects.

Higher loading capacities are to be expected when the administered drug is incorporated into the microspheres during the actual process of microsphere manufacture. It is known that for many peptides and proteins the amount of drug substance to be administered for the resultant therapeutic effect will be of the order of a few milligrams, micrograms, nanograms or less. Microcapsules of a similar size, which are bioadhesive and which have controlled release properties, would also be expected to provide similar benefit in terms of an increased and modified bio-availability of administered drugs. These microcapsules can be produced by a variety of methods. The surface of the capsule may be adhesive in its own right or may be modified by coating methods familiar to those skilled in the art. These coating materials are preferably bio-adhesive polymers such as polycarbophil, carbopol, DEAE-dextran or alginates. These microcapsules are deemed to be "microspheres" for the purposes of this specification and again, are preferably 10–100 μm in diameter.

It has been found that compositions of the invention have the ability to enhance greatly the bioavailability of polar compounds. The use of microspheres in preferred compositions of the invention is believed to provide for greater retention of the delivery systems in the nasal cavity and may also afford protection of the active compound against degradation by enzymes.

The compositions may be used with active compounds selected from the following non-exclusive list: insulin*, calcitonins (for example porcine, human, salmon, chicken or eel) and synthetic modifications thereof*, growth hormones, glucagon, interferons (especially alpha 2 interferon for treatment of common colds), secretin, bradykinin antagonists, growth hormone releasing factor, thyrotropin releasing hormone, ACTH analogues, insulin-like growth factors, enkephalins*, LHRH and analogues* (Nafarelin, Buserelin, Zolidex), GHRH (growth hormone releasing hormone)*, nifedipin, THF(thymic humoral factor)*, CGRP (calcitonin gene related peptide)*, atrial natriuretic peptide*, antibiotics, metoclopramide*, ergotamine*, dihydroergotamine, ergometrine, Pizotizin*, nasal vaccines (particularly AIDS vaccines, measles, rhinovirus Type 13 and respiratory syncitial virus)*, Factor VIII, pentamidine, CCK* (cholecystokinin), desmopressin* (and DDAVP analogues ) and vasopressin*.

Preferably the active compound used in the composition has a molecular weight of at least 500 or 1000. The starred compounds are especially preferred for administration with the microsphere system of the invention, especially insulin, calcitonin, CCK, desmopressin and vasopressin. The insulin may be isolated from natural sources, for example pigs, but more preferably is genetically engineered human insulin.

Further drugs include: antibiotics and antimicrobial agents such as tetracycline hydrochloride, leucomycin, penicillin, penicillin derivatives, erythromycin, sulphathiazole and nitrofurazone; local anaesthetics such as benzocaine; vasoconstrictors such as phenylephrine hydrochloride, tetrahydrozoline hydrochloride, naphazoline nitrate, oxymetazoline hydrochloride and tramazoline hydrochloride; cardiotonics such as digitalis and digoxin; vasodilators such as nitro-glycerine and papaverine hydrochloride; antiseptics such as chlorhexidine hydrochloride, hexylresorcinol, dequaliniumchloride and ethacridine; enzymes such as lysozyme chloride, dextranase; bone metabolism controlling agents such as vitamin D, and active vitamin $D_3$; sex hormones; hypotensives; sedatives; antitumour agents; steroidal anti-inflammatory agents such as hydrocortisone, prednisone, fluticasone, prednisolone, triamcinolone, triamcinolone acetonide, dexamethasone, betamethasone, beclomethasone, and beclomethasone dipropionate; non-steroidal anti-inflammatory agents such as acetaminophen, aspirin, aminopyrine, phenylbutazone, mefanamic acid, ibuprofen, diclofenac sodium, indomethacine, colchicine, and probenocid; enzymatic anti-inflammatory agents such as chymotrypsin and bromelain seratiopeptidase; anti-histaminic agents such as diphenhydramine hydrochloride, chloropheniramine maleate and clemastine; anti-allergic agents; and antitussive-expectorant antasthmatic agents such as sodium chromoglycate, codeine phosphate, and isoproterenol hydrochloride.

The compositions are generally made up in known ways suitable for the mucosa concerned, for example the nose or vagina. Sterile, physiologically acceptable diluents may be used, for example sterile saline solution.

When the compositions of the invention comprise insulin, they are useful for treating diabetics. Calcitonin-containing compositions are useful for treating disorders of calcium metabolism, for example osteoporosis.

The invention will now be described by way of example, with reference to the accompanying drawings, in which:

A BRIEF DESCRIPTION OF THE DRAWINGS

Figure 1:
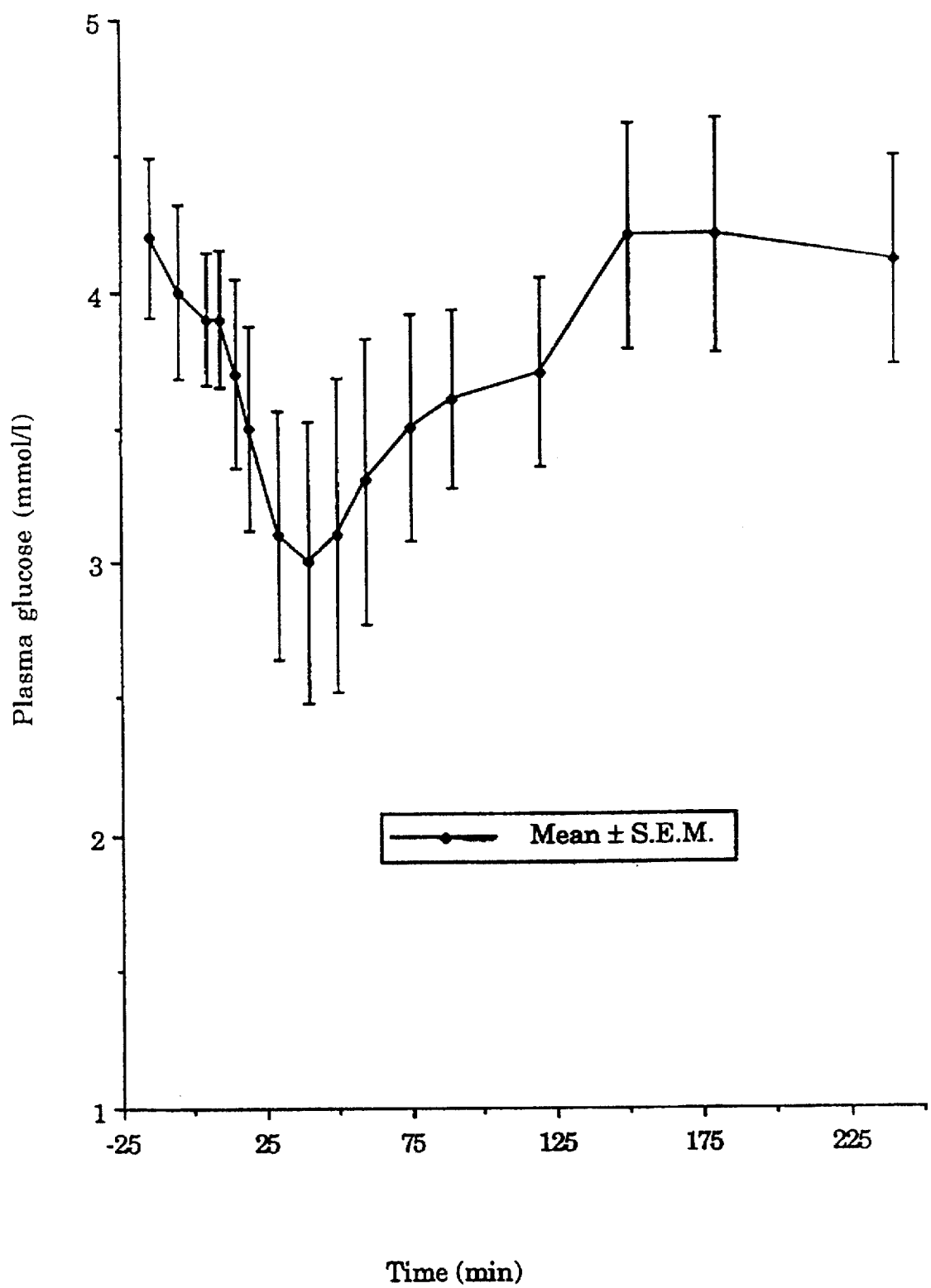
FIG. 1 is a plot of plasma glucose (m mol/l) against time for sheep, following nasal administration of 2.0 IU/kg insulin plus 0.02 mg/kg LPG in solution.
Figure 2:
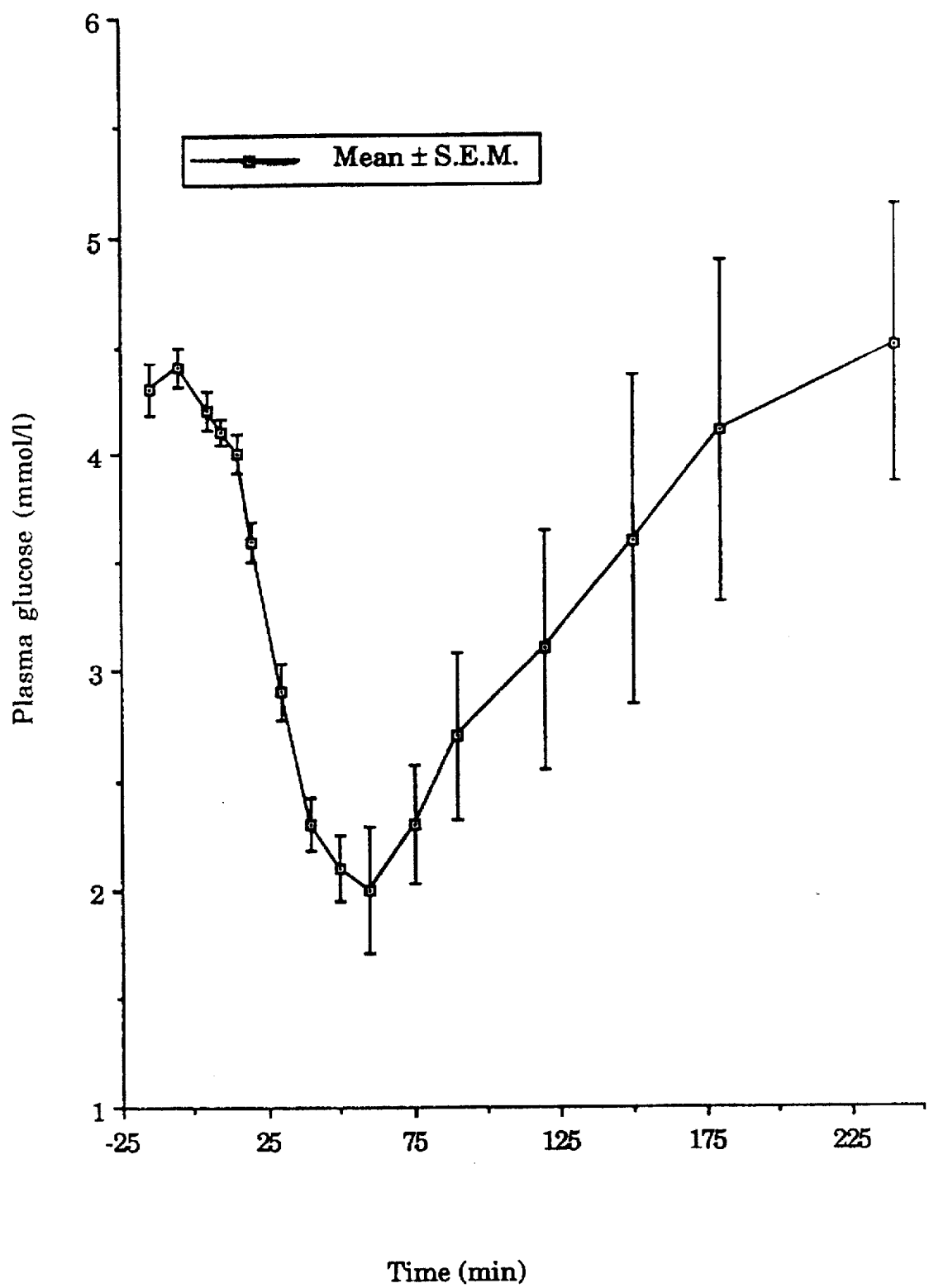
FIG. 2 is a plot of plasma glucose (m mol/l) against time for sheep, following nasal administration of 2.0 IU/kg insulin plus 2.5 mg/kg SMS and 0.2 mg/kg LPG as a lyophilised powder.
Figure 3:
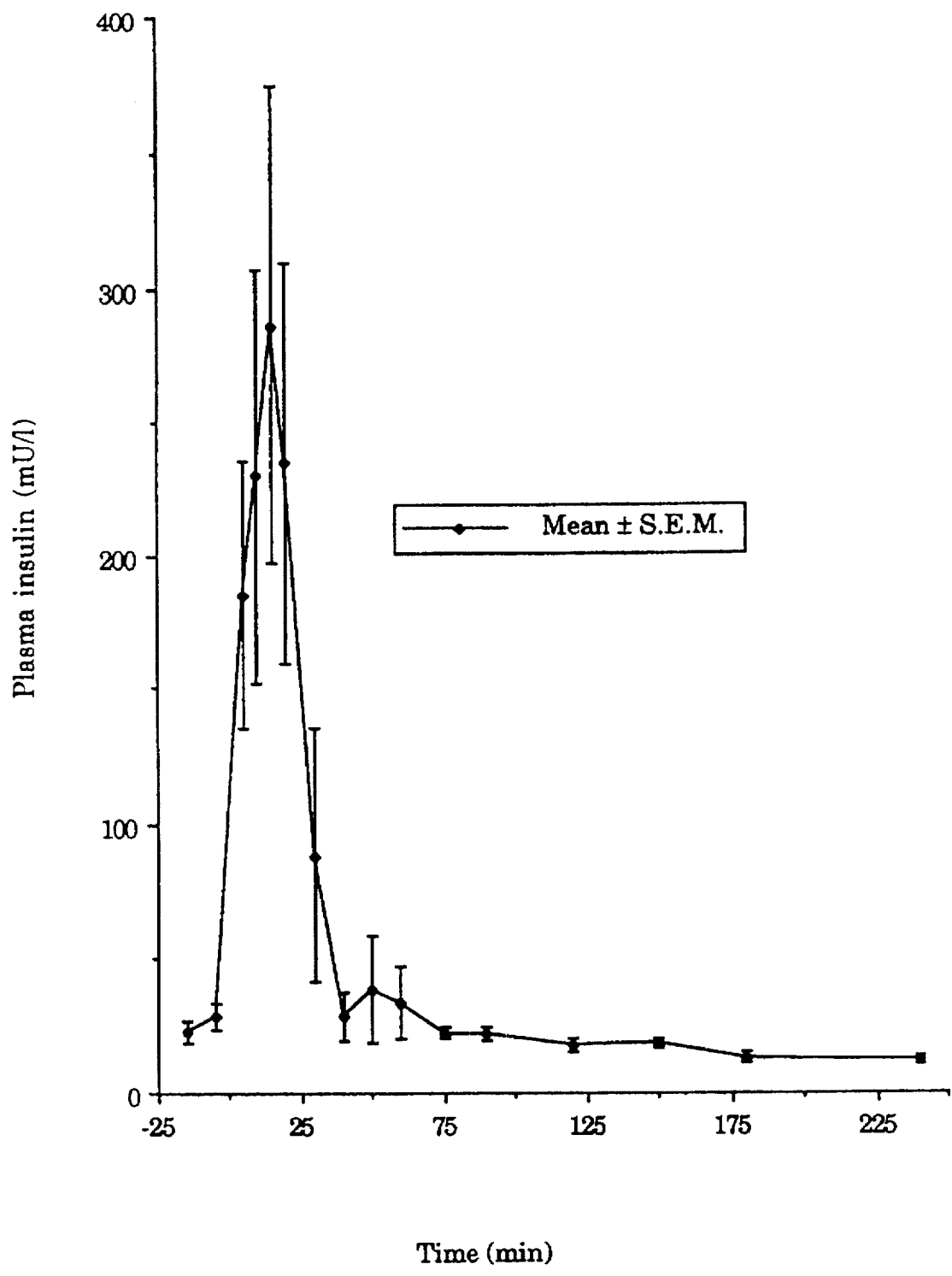
Figure 4:
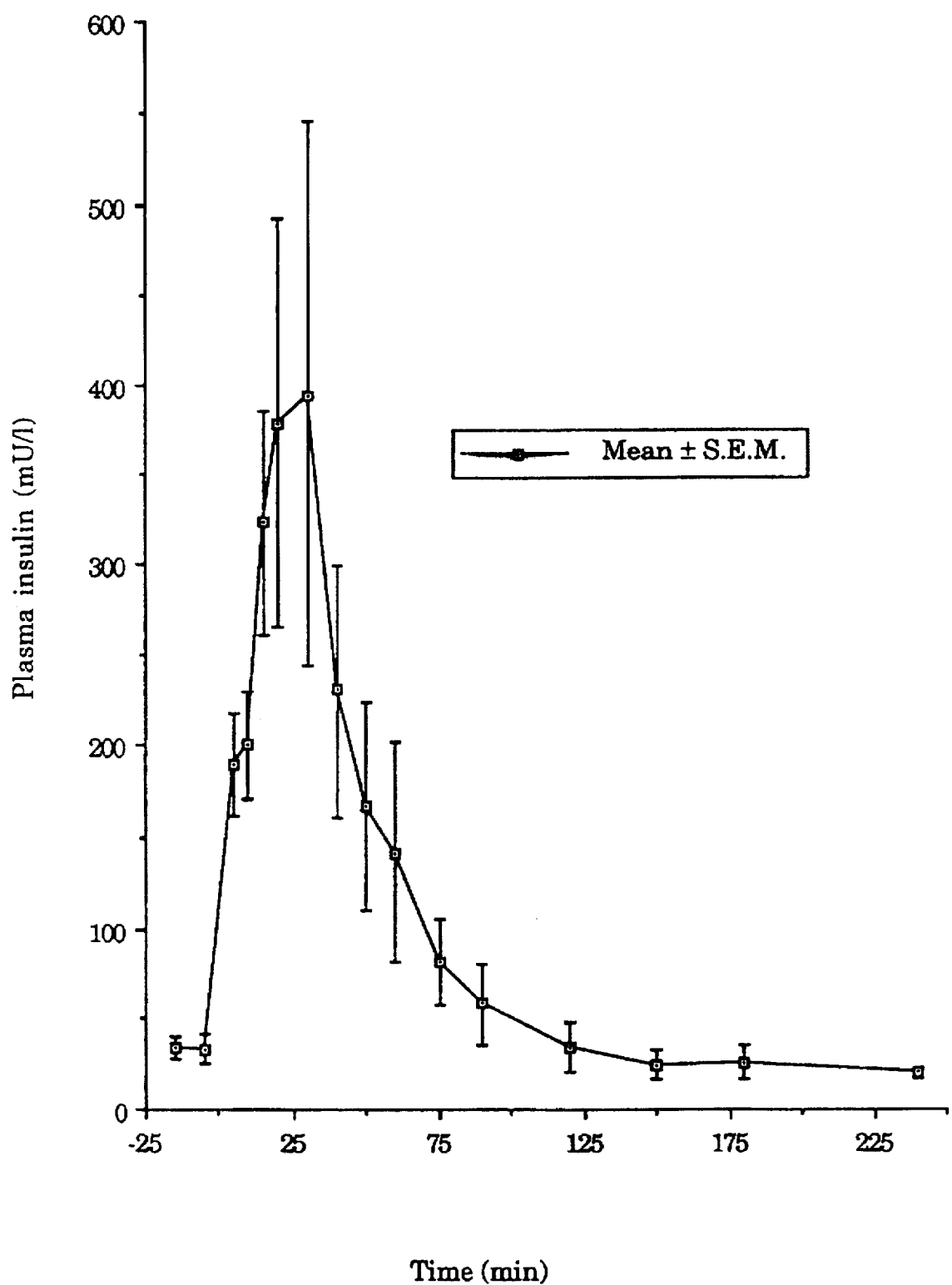
Figure 5:
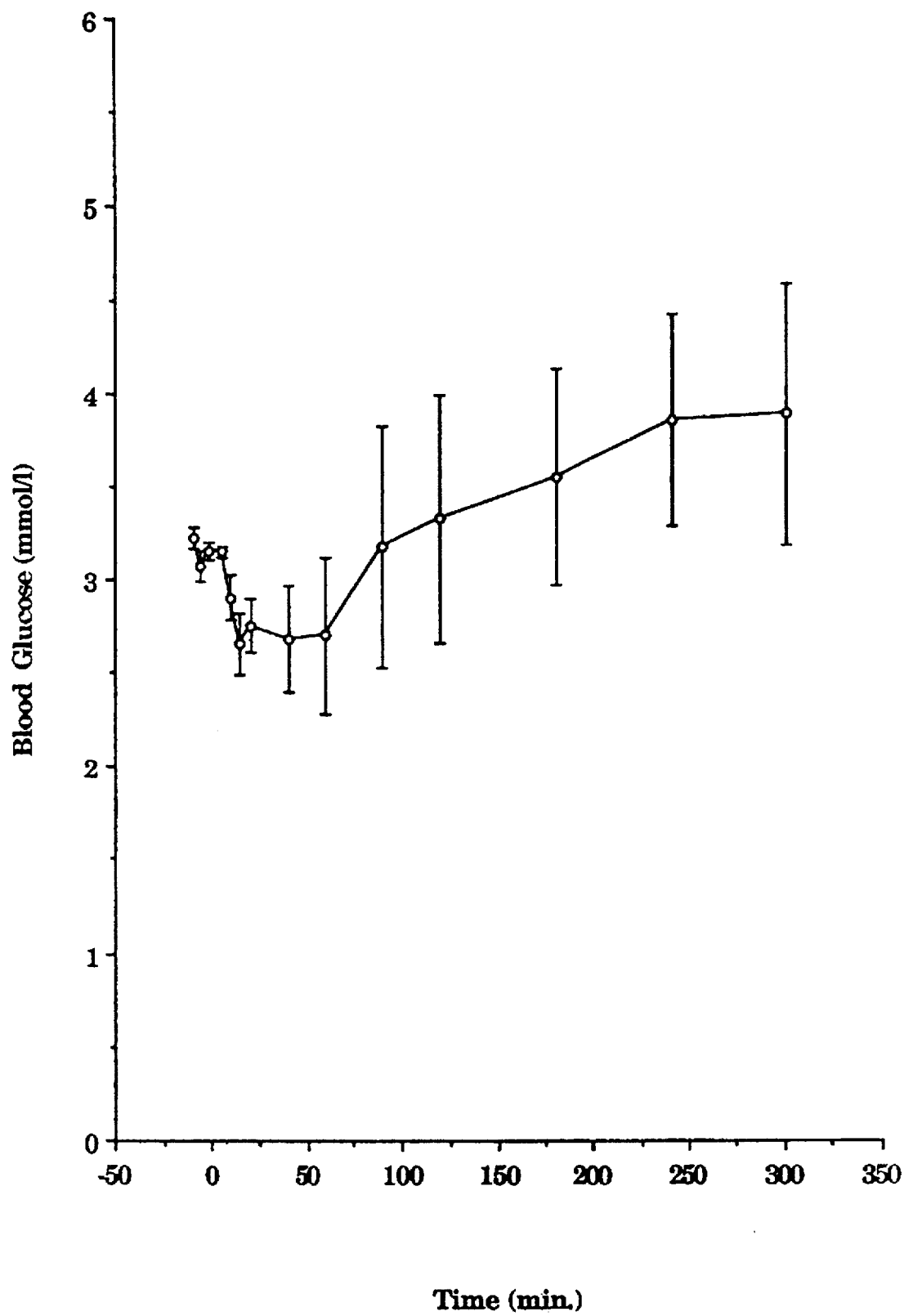
Figure 6:
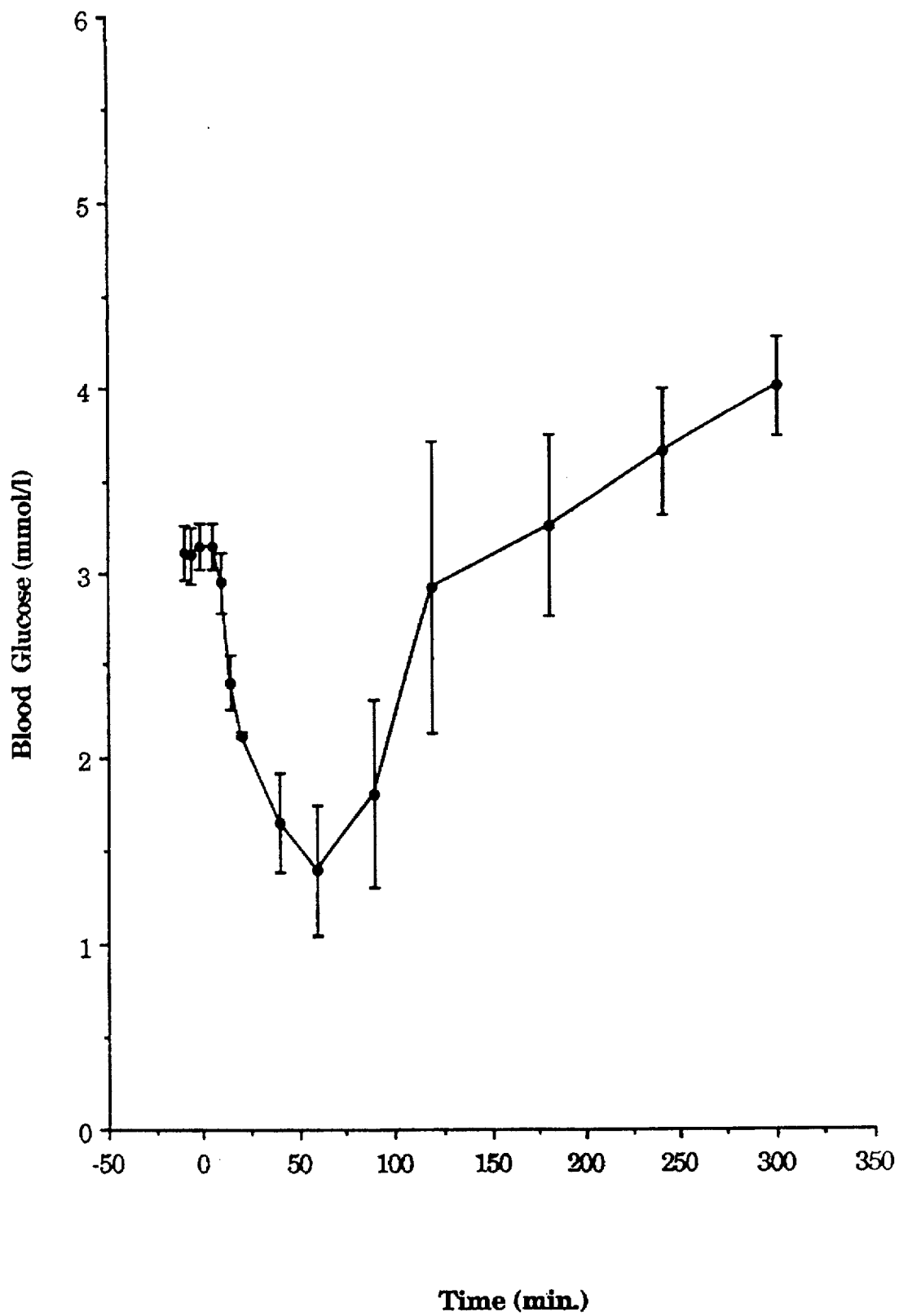
Figure 7:
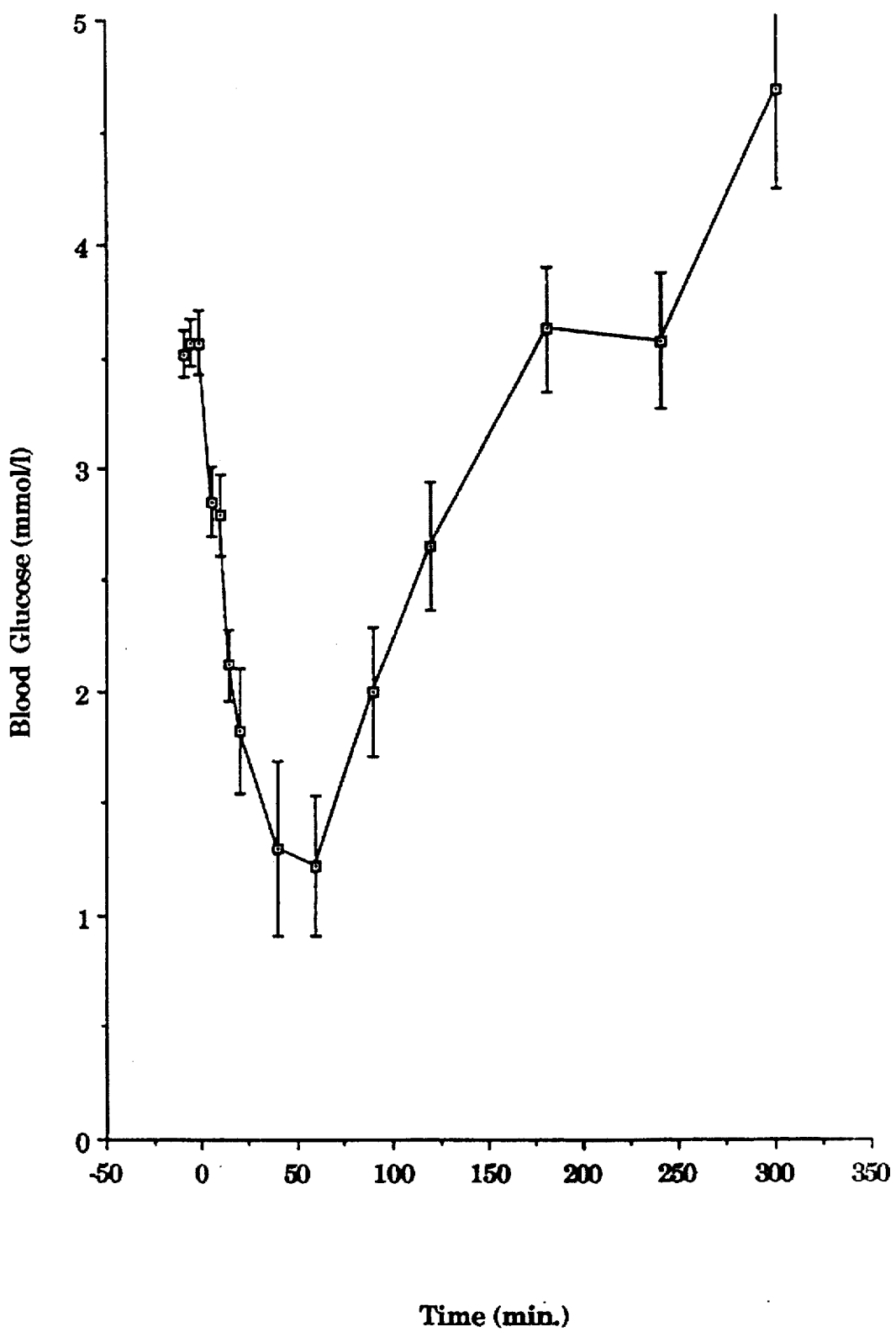
Figure 8:
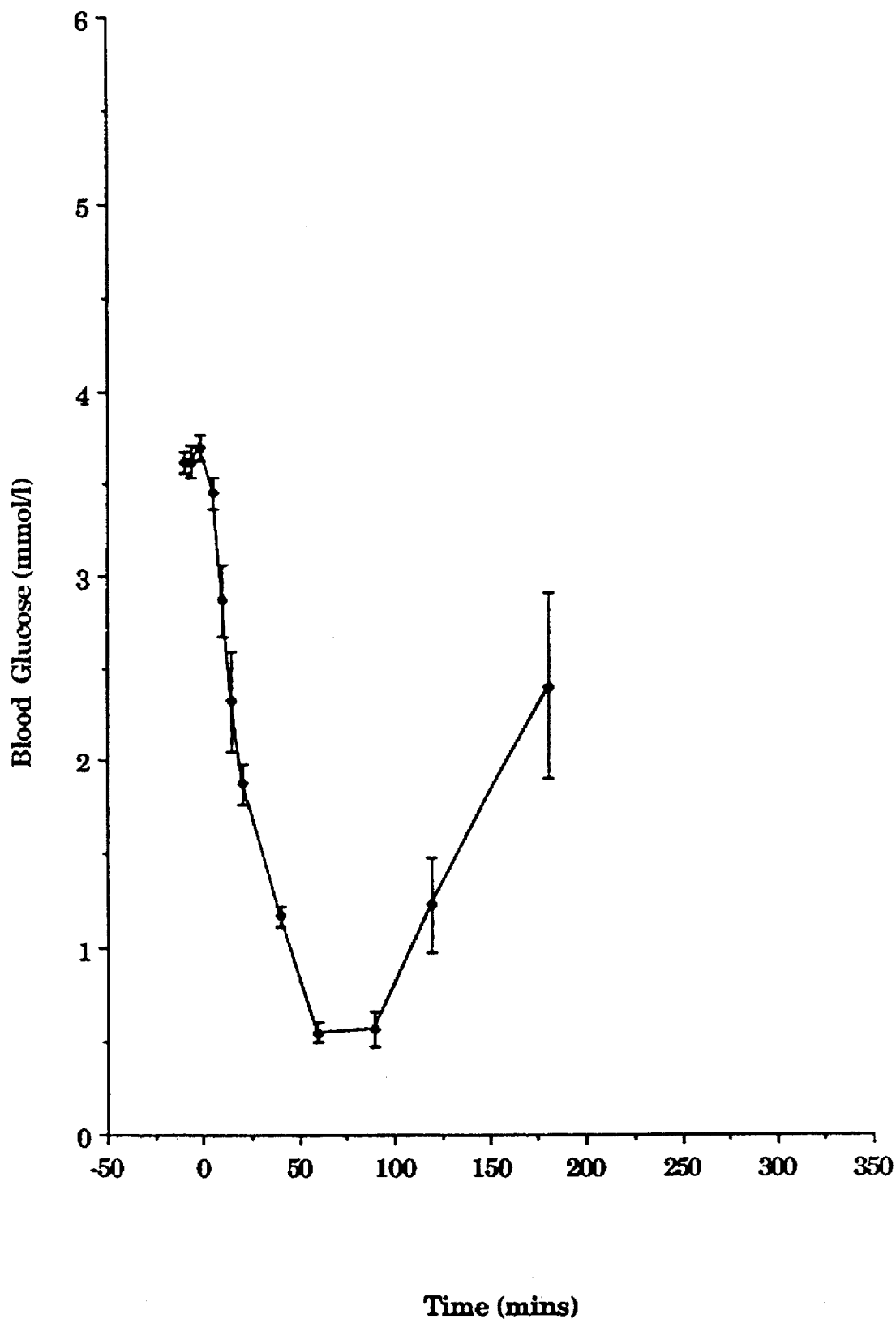
Figure 9:
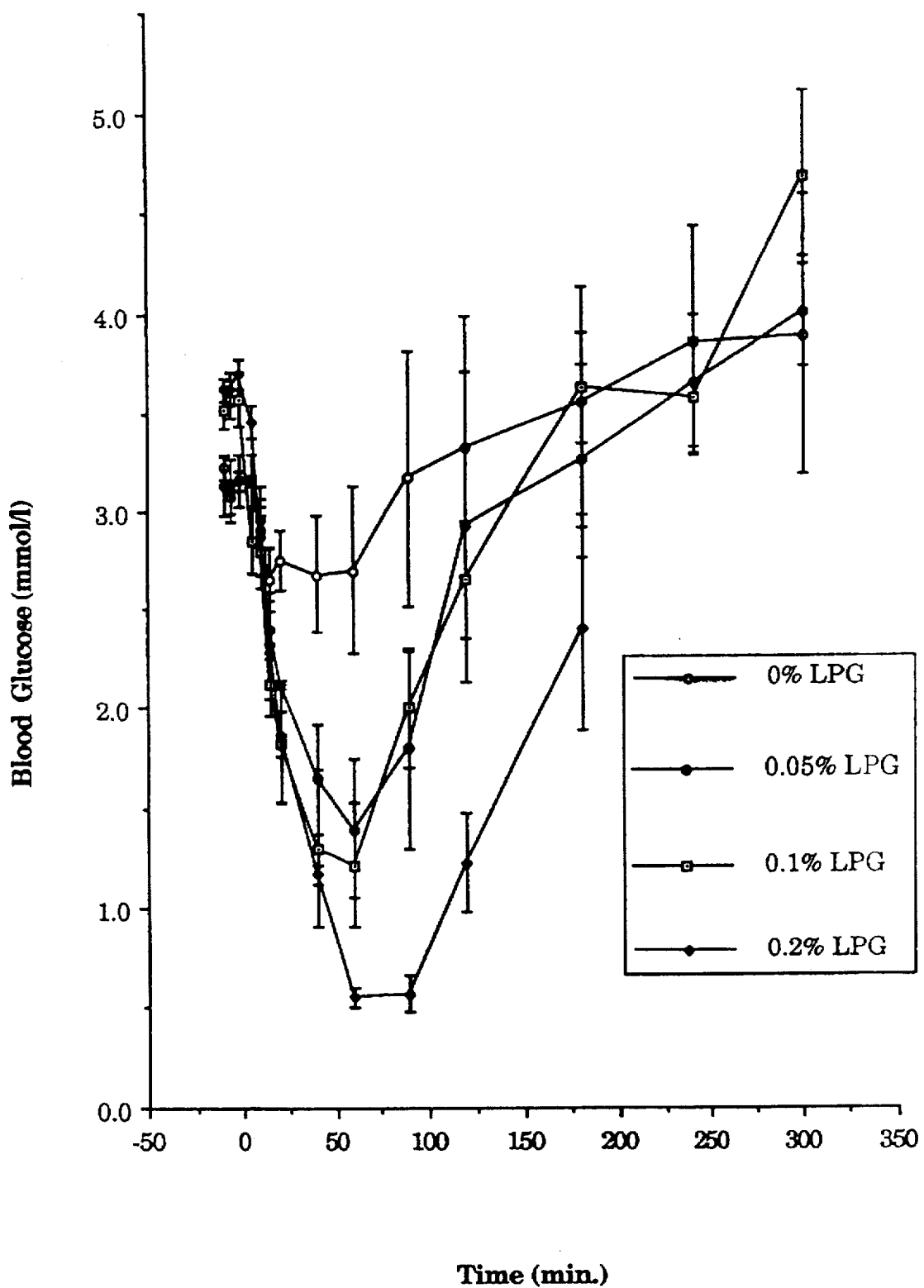
Figure 10:
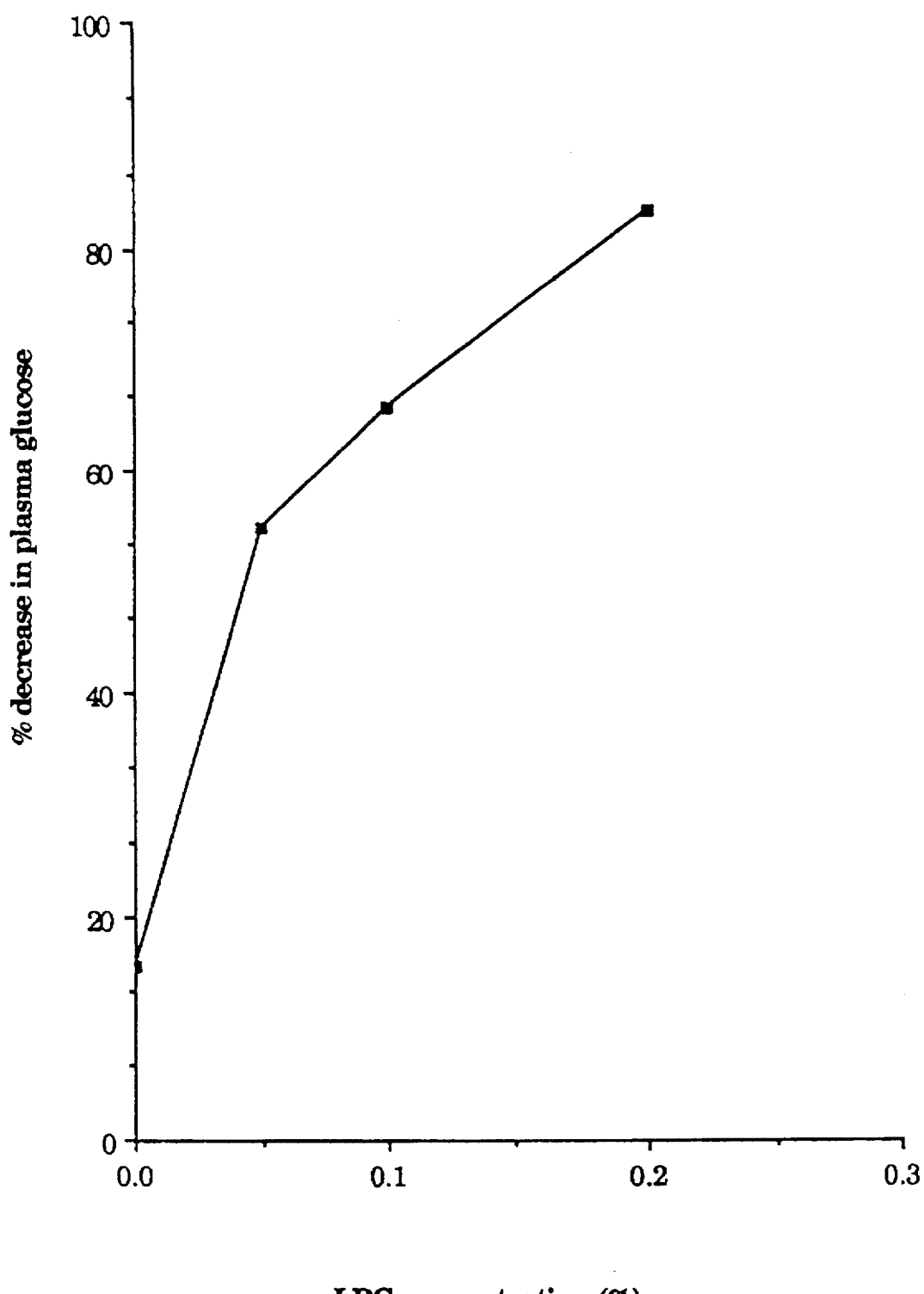
Figure 11:
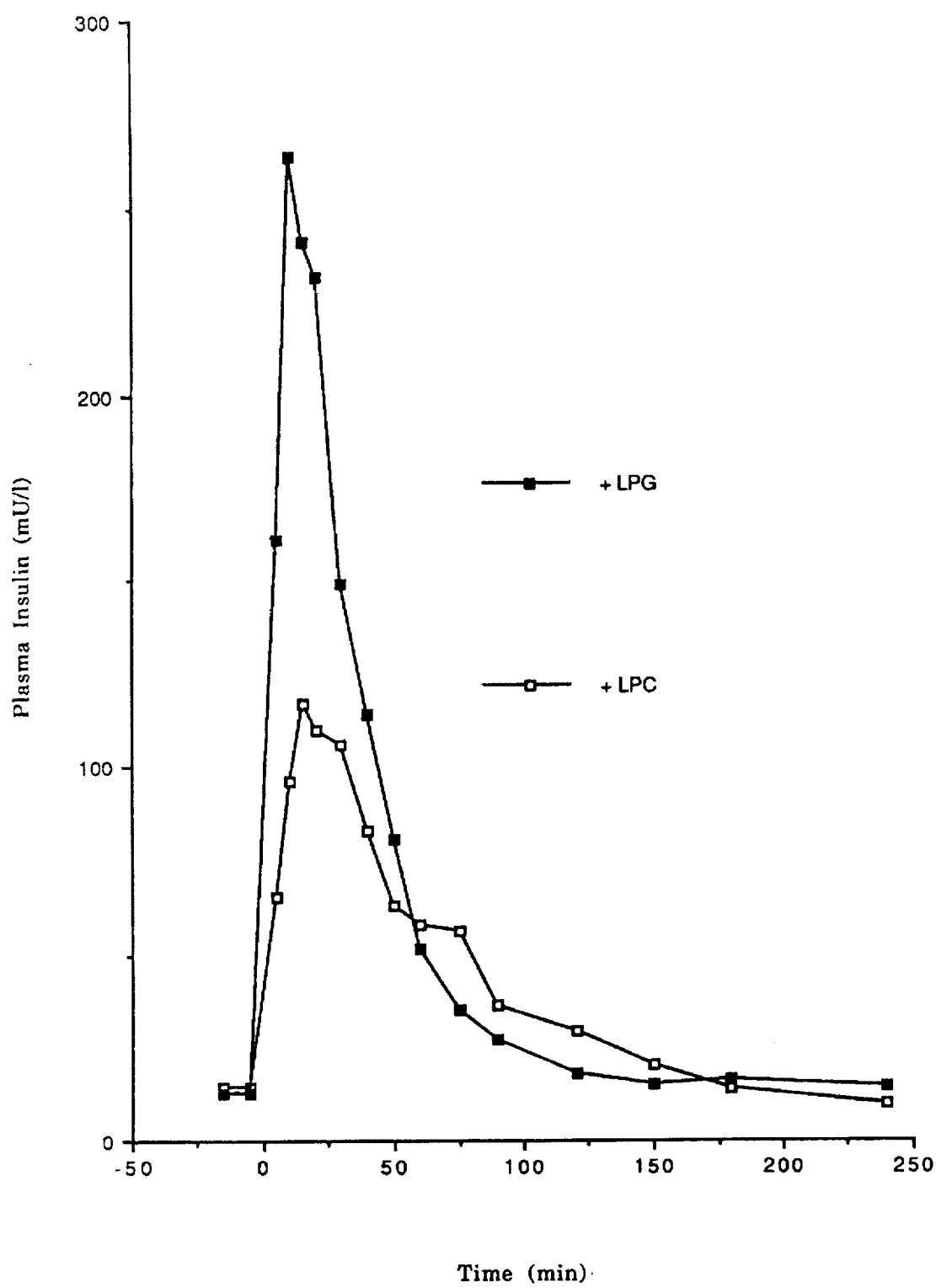
Figure 12:
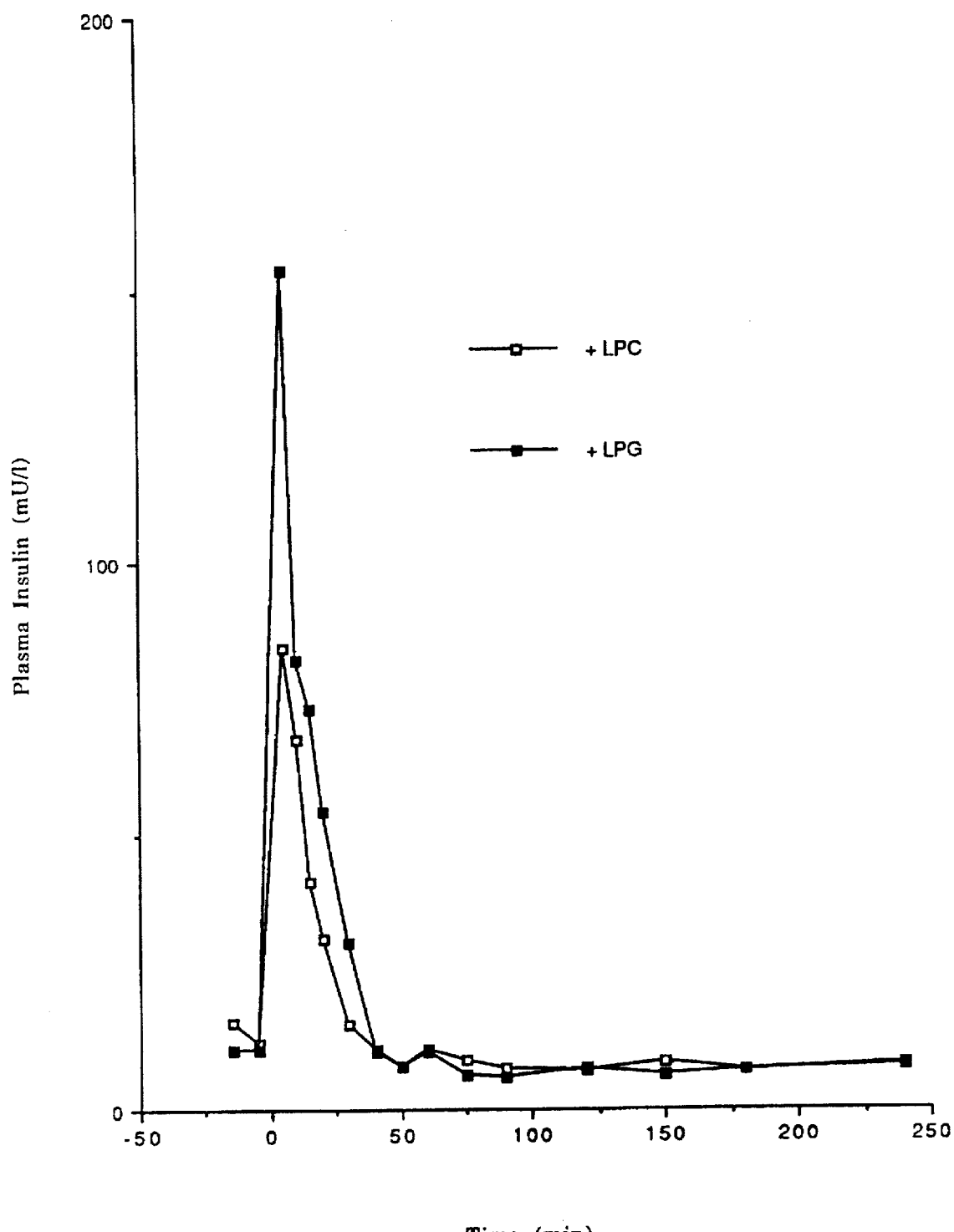

FIG. 3 corresponds to FIG. 1 but shows plasma insulin levels (m U/l);

FIG. 4 corresponds to FIG. 2 but shows plasma insulin levels (m U/l);

FIG. 5 is a plot of blood glucose (m mol/l) against time for rats, following nasal administration of 8 IU/kg in solution;

FIG. 6 corresponds to FIG. 5 but the solution additionally contained 0.05% LPG;

FIG. 7 corresponds to FIG. 5 but the solution additionally contained 0.10% LPG;

FIG. 8 corresponds to FIG. 5 but the solution additionally contained 0.20% LPG;

FIG. 9 is a superimposed plot of FIGS. 5 to 8;

FIG. 10 shows the relationship between LPG concentration and maximal decrease in blood glucose levels, based on the data of FIGS. 5 to 8;

FIG. 11 shows the plasma insulin levels with LPC or LPG enhanced lyophilised formulations; and FIG. 12 corresponds to FIG. 11 but relates to solutions.

EXAMPLE 1

INTRANASAL ADMINISTRATION OF Na-INSULIN IN SHEEP

The effect of lysophosphatidylglycerol (LPG) on the nasal delivery of insulin from aqueous solutions, and from lyophilised powders in combination with starch microspheres, was assessed.

Materials: Semi-synthetic human Na-insulin supplied by Nordisk Gentofte (Batch No. P371) was used. The water content of the sample was determined by spectrometry at the time of its use to be 13.2%. Lysophosphatidylglycerol (Sigma L1756) was used as the enhancer.

Sheep: Six cross-bred (Suffolk and Texel) sheep of known weight were used. The animals were not fasted prior to insulin administration. An in-dwelling Viggo secalon cannula of 1.2 mm i.d., fitted with a secalon universal flow-switch, was placed approx. 15 cm into one of the external jugular veins of each animal on the first day of the study and, whenever necessary, was kept patent by flushing it with heparinised normal saline (25 IU/ml). This cannula was removed upon the completion of the study.

Preparation of insulin formulations: Insulin solutions were prepared in phosphate buffer (pH 7.3) according to the manufacturer's instructions.

Administration of insulin formulations: The sheep were divided into 2 groups of 3 animals each. Group 1 received 2.0 IU/kg insulin and 0.02 mg/kg LPG in the form of an aqueous buffered (pH 7.3) solution of 160 IU/ml insulin and 1.6 mg/ml LPG. Group 2 received 2.0 IU/kg insulin together with 2.5 mg/kg SMS and 0.2 mg/kg LPG, in the form of a lyophilised powder.

Further details of study: For the intranasal studies, it was necessary to sedate the sheep by use of an i.v. dose of ketamine hydrochloride at 2.0 mg/kg. This was intended as a counter-measure against the animal sneezing during administration. The anaesthesia lasted for about 3 minutes. Blood samples of 5 ml were collected onto crushed ice from the cannulated jugular vein of the sheep at 15 and 5 min prior to the insulin administration and at 5, 10, 15, 20, 30, 40, 50, 60, 75, 90, 120, 150, 180, and 240 min post-administration. Each blood sample was divided into two parts. For insulin analysis, the blood collected (3.0 ml) was mixed gently in 5 ml heparinised (Li Heparin) tubes. For glucose analysis, the blood collected (2.0 ml) was mixed gently in 5 ml sodium fluoride tubes. The plasma was collected by centrifugation at 4° C. and 3000 rpm, and then stored at −20° C. awaiting insulin and glucose analysis.

The mean weight of the sheep (±S.D.) was 40.3 kg

| Formulation | Mean AUC (mU · min/l) | S.E.M. |
|---|---|---|
| Na-SHI + SMS + 0.2 mg/kg LPG | 17754 | 5725 |
| Na-SHI + 0.02 mg/kg LPG in sol. | 7399 | 2139 |

The results are shown in FIGS. 1 to 4.

EXAMPLE 2

EFFECT OF LYSOPHOSPHATIDYLGLYCEROL CONCENTRATION ON THE NASAL ABSORPTION OF INSULIN IN RATS

The effect of different concentrations of LPG on the nasal absorption of insulin in rats was assessed.

Materials: Semisynthetic human Na-insulin (P371); the water content of the insulin powder was determined by spectrophotometry to be 15%. L-α-Lysophosphatidyl-DL-glycerol (Sigma L-1756).

Preparation of insulin solutions: A phosphate buffer of pH 7.3–7.4 was prepared by weighing 0.476 g of $Na_2HPO_4.2H_2O$ and 0.1537 g of $NaH_2PO_4.2H_2O$ and making up to 250 ml with distilled water. An insulin solution of double-strength (160 IU/ml) was prepared freshly in the phosphate buffer. LPG solutions were also prepared at double-strength in the buffer solution. The above were then mixed in a 1:1 ratio to produce a final solution of 80 IU/ml insulin containing the required concentration of LPG.

Animal Model: The rat in vivo experimental model described by Hirai et al (Int. J. Pharm., 7, 317–325, 1981) and modified by Fisher et al (J. Pharm. Pharmacol., 39, 357–362, 1987) was used to study the effect of concentration of lysophosphatidylglycerol (LPG) on the intranasal absorption of insulin solutions.

Non-diabetic male Wistar rats (JABU, Sutton Bonington, U.K.) of about 200 g were fasted overnight for about 20 hours prior to the study. These were then anaesthetized by i.p. injection of 60 mg/kg of pentobarbitone (60 mg/ml, Sagatal, May and Baker). The rats were tracheotomized, the oesophagus sealed and the carotid artery cannulated. 20 μl of the insulin solution containing 80 IU/ml Of the drug with or without enhancer was instilled into the nasal cavity, using a Hamilton microsyringe fitted with Portex tubing. The dose of insulin was thus 8 IU/kg. Blood samples (150 ul) were collected in fluoride oxalate blood tubes from the carotid artery at 10, 6, and 2 min prior to drug administration and at 5, 10, 15, 20, 40, 60, 90, 120, 180, 240 and 300 min post-administration. The samples were kept on crushed ice and assayed for glucose content on the day of the study. The glucose level was determined by the glucose oxidase method on a Yellow Springs 23AM glucose analyser.

Administration of insulin formulations: The rats were divided into 4 groups of 4 animals each and the following formulations were investigated. 1. Intranasal administration of an aqueous buffered solution containing 80 IU/ml insulin and 0.0% LPG (i.e. a control solution). 2. Intranasal administration of an aqueous buffered solution containing 80 IU/ml Insulin and (A) 0.05% LPG
(B) 0.10% LPG
(C) 0.20% LPG The results are shown in FIGS. 5 to 10.

EXAMPLE 3

VAGINAL TOXICOLOGY

Materials: 17-β-oestradiol (Sigma Chemical Company Ltd., Dorset, U.K.) was prepared as a solution in arachis oil at a concentration of 100 μg/ml.

Semi-synthetic human sodium-insulin was obtained as a gift from Novo-Nordisk (Denmark) and prepared as a solution in phosphate buffer, pH 7.3 to 7.4, at a concentration of 20 IU/ml. The water content of the insulin sample was determined by spectrofluorimetric analysis of the prepared solution. By convention, a 1 mg/ml (28 IU/ml) insulin solution in a 1 cm cuvette absorbs 1.058 at 276 nm. Thus, the water content was found to be 14% and the weight of the insulin used was adjusted accordingly.

In some experiments, absorption enhancers were added separately to the insulin solutions at the following concentrations: 0.5% L-α-lysophosphatidylcholine (LPC) and 0.5% L-α-lysophosphatidyl-DL-glycerol (LPG) (Sigma Chemical Company Ltd., Dorset, U.K.). All other chemicals used were of reagent grade.

Vaginal administration of insulin and enhancers to rats

Female Wistar rats (JABU, Sutton Bonington, U.K.) weighing approximately 200 g, were bilaterally ovariectomised under halothane anaesthesia. The operation wounds were closed with Michel clips which were removed after 10 days. The animals were allowed to recover for at least two weeks before receiving further treatment. Twenty-four hours prior to drug absorption studies, 100 μl of oestradiol solution (approximately 40 μg/kg) was administered by subcutaneous injection.

After fasting overnight, groups of rats (n=4–7) were anaesthetised by intra-peritoneal injection of 60 mg/kg pentobarbitone sodium (60 mg/ml, Sagatal, May and Baker). After tracheotomy and cannulation of the carotid artery and jugular vein to allow removal of blood samples and replacement of blood volume with saline, respectively, the rats were prepared for vaginal dosing. Initial blood samples (100 μl) were collected 15 mins and 5 mins prior to drug administration in fluoride oxalate tubes (Sterilin, Northern Media). Insulin solutions were instilled into the vaginal tract (8 IU/400 μl/kg) and blood samples were taken at intervals over four hours. All samples were stored at 4° C. prior to analysis within four hours. Blood glucose levels were determined by the glucose oxidase method using a Yellow Springs Instrument 23 AM analyser, calibrated for glucose measurement in the range 0 to 10 mmol/l.

The areas under the curves (AUCs) of blood glucose concentrations from 0 to 120 minutes were determined and the differences between each treatment group were assessed by the use of the Student's t-test.

At the end of the absorption experiments, after 2 to 4 hours, the rats were sacrificed by an overdose of pentobarbitone sodium and the vaginal tissues were removed and placed in fixative for histology. In addition, a control group of rats were prepared. They were treated in a similar manner to the experimental group but did not receive a vaginal enema.

Histological study: The tissues were fixed in Bouin Hollande fluid and processed by conventional steps for histological examination. The thickness of the vaginal epithelium in the control group of rats was quantitatively assessed as follows. Five sections from each animal were randomly selected from a group of nine sections collected through the length of each organ. The thickness of the vaginal epithelium was measured by means of an eye-piece graticule at five sites of each section. Hence, 25 measurements were made for each rat and the data expressed as a mean epithelial thickness.

Results

The vaginal epithelium of the control group had a mean thickness of 41 μm (SEM 1 μm) and consisted of a basal layer of cuboidal cells covered by several flattened layers of squamous cells and an outer layer of cuboidal cells. The effect of insulin and enhancer formulations on the histology of this vaginal epithelium was investigated.

After vaginal administration of insulin solution alone, the surface epithelium was unchanged, except that in one animal there was some loss of the surface layer. Vaginal administration of insulin +LPC solution resulted in various histological changes which were mainly confined to the outer cell layers. The surface cuboidal cell layer was often disrupted or lost and underlying squamous cells were altered with dense nuclei and eosinophilic cytoplasms. In two of the six tissue samples examined, deeper layers of the epithelium were affected with areas of complete loss of cellular structure with a hyaline-like residue remaining.

Treatment with insulin +LPG solution did not result in such severe epithelial damage. In many areas, the vaginal epithelium closely resembled that of the control group. However, in some areas the outer cell layers showed signs of disruption with cells shed into the vaginal lumen.

EXAMPLE 4

NASAL TOXICOLOGY

The nasal administration of insulin in buffer (pH7.4) resulted in increased mucus discharge in the dosed side of the cavity and a slight reduction in cell height when compared to the undosed side. Cilia appeared unaffected on both sides. Any effects were restricted to the septal region with turbinates apparently unchanged. Mucus discharged from goblet cells was usually still adjacent to the luminal surface of the septal epithelium and not dispersed into the rest of the cavity indicating the low volumes involved.

There was mucus present in the undosed cavity of a few animals, though again this was generally adjacent to the septum. One animal in particular had mucus visible in both sides of the cavity. Perfusion had not been very successful in this case however, judging by distribution of yellow fixative, and the cavities had been flushed retrogradely with Bouin Hollande solution via the tracheal cannula to ensure good fixation. This procedure may have physically disrupted goblet cells or caused a reflex discharge of mucus prior to the fixative action and both sides would have been affected.

The effects of insulin in final phosphate buffer therefore, were a relatively small degree of mucus discharge with accompanying slight reduction in respiratory epithelial cell height on the nasal septum.

More severe effects were observed in nasal sections on the animals treated with insulin in combination with LPC. Increased amounts of mucus were present in the body of the dosed cavity, including around the turbinates in some cases. Surface cell loss had occurred from the septum and turbinates. Epithelial cells had undergone rearrangement with remaining nuclei packed towards the basement membrane. The pseudostratified appearance was lost and epithelium height greatly reduced. Some cilia were still present on intact respiratory epithelial cells. Alcian blue stained sections showed that some mucus remained in the cell interiors but the decreased cell height was clear; where only a thin, simple epithelial layer remained however, the cells were completely devoid of mucus.

The undosed 'control' side of the cavity was generally unaffected except for some mucus discharge onto the septal surface or into the dorsal meatus.

The effects of the LPG/insulin formulation on the nasal mucosa were less severe than those of the LPC enhancer. In most places the tissue appeared very similar to the control, however in some places a few cells lost from the septum and turbinates were visible in the dosed cavity and mucus discharge on this side resulted in a slight decrease in epithelium height. The clear cell structure was not as well defined as on the undosed side and cytoplasmic space appeared reduced.

EXAMPLE 5
COMPARATIVE EXAMPLE

In experiments similar to those of Example 1 above, L-αlysophosphatidylcholine (LPC) was compared with L-α-lysophosphatidyl-DL-glycerol (LPG) for use as enhancers with starch microspheres.

The sheep were divided into 4 groups of 5 animals each. Group 1 received 2.0 IU/kg insulin together with 2.0 mg/kg SMS 45/25 microspheres (Pharmacia) and 0.2 mg/kg LPC (Formulation 1) intranasally in the form of a lyophilised powder. A sheep of 50 kg thus received 100 IU of insulin together with 100 mg SMS 45/25 microspheres and 10.0 mg LPC. Group 2 received 2.0 IU/kg insulin together with 2.0 mg/kg SMS 45/25 microspheres and 0.2 mg/kg LPG Formulation 2) intranasally in the form of a lyophilised powder. A sheep of 50 kg thus received 100 IU of insulin together with 100 mg SMS 45/25 microspheres and 10.0 mg LPG. Group 3 received 2.0 IU/kg insulin together with 0.02 mg/kg LPC (Formulation 3) intranasally in the form of a solution at 0.01 ml/kg. A sheep of 50 kg thus received 100 IU of insulin together with 1.0 mg LPC in a volume of 0.5 ml. Group 4 received 2.0 IU/kg insulin together with 0.02 mg/kg LPG (Formulation 4) intranasally in the form of a solution at 0.01 ml/kg. A sheep of 50 kg thus received 100 IU of insulin together with 1.0 mg LPG in a volume of 0.5 ml. For intranasal administration of the powdered formulations (Groups 1 and 2), a Leymed red rubber Magill's tube oral of 6.5 mm was loaded with the powder formulation and then inserted into the nostril of the sheep to a preset depth of 6 cm before blowing the powder into the nasal cavity. For the intranasal administration of solution formulations (Groups 3 and 4), a blueline umbilical cannula of 35 cm length (size 6FG, Portex) was inserted into one of the nostrils of the sheep to a preset depth of 10 cm before the delivery of half the required solution from a 1 ml syringe. The process was then immediately repeated using the other nostril.

Sedation/Blood Sampling: For the intranasal studies, the sheep were sedated by use of an i.v. dose of ketamine hydrochloride (Ketalar (Regd. T.M.), 100 mg/ml injection) at 2.25 mg/kg. This was intended for animal restraint and also as a counter-measure against the animal sneezing during administration. The anaesthesia lasts for about 3 minutes. Blood samples of 6.0 ml were collected onto crushed ice from the cannulated jugular vein of the sheep at 15 and 5 min prior to the insulin administration and at 5, 10, 15, 20, 30, 40, 50, 60, 75, 90, 120, 150, 180 and 240 min post-administration. Each blood sample was divided into two parts and analysed as in Example 1.

The results, shown in FIGS. 11 and 12, demonstrated that, in terms of plasma insulin levels, LPG was superior to LPC. Plasma glucose levels also were lower (i.e. better) with LPG.

EXAMPLE 6

PREPARATION OF MICROSPHERES

Gelatin. (Simple coacervation, non crosslinked microspheres, size 75±8 μm). 5 g of acid ossein gelatin (pI 6.8, Bloom 259, Croda Gelatins, UK) was soaked for 24 hours and then dissolved in 30 ml of distilled water at 50° C. NaOH 1% (w/v) was added until the pH reached a value of 6.8 and the system was made up to 50 ml with further distilled water. At 50° C., PEG 4000 30% (w/v) solution was added (approximately 20 ml) until the coacervate region was reached. To control this step, a nephelometer was used. The beaker was then cooled on an ice-bath during constant mechanical stirring at 450 rpm for 15 minutes. 20 ml of isopropanol was then added and the microspheres were centrifuged, decanted, filtered and freeze-dried. This method may be adapted for use with other proteins and peptides, such as albumin and insulin.

Soluble potato starch. (Phase separation, non crosslinked particles prepared by Hella). 7 ml of PEG 30% solution was added to 15 ml of filtered (filter glass number 1) 5% (w/v) soluble potato starch, pH 7 at 70° C. to produce phase separation. The particles were isolated by centrifugation, filtration and then freeze-dried.

Insulin. (Phase separation, particles). PEG 4000 as a solid (3.5 g) was added to 10 ml of 2.5% w/v zinc solution pH 7.5 until phase separation and formation of particles. At different pH different amount of PEG are required to precipitate insulin. In fact pH is a more efficient factor as precipitant agent than PEG is.

Sometimes, albumin and gelatin microspheres are obtained as clumps of microspheres which usually stick together. To break the clumps without breaking the microspheres, they are first freeze-dried (so the size is reduced) and then separated with the use of sieves until the required size of microspheres is obtained.

I claim:

1. A drug delivery system comprising a pharmacologically active compound and an absorption enhancer in a solution formulated for administration to mucosal surfaces, wherein the absorption enhancer is a lysophosphatidyl glycerol of the general formula I

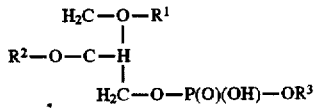

wherein one of $R^1$ and $R^2$ is hydrogen and the other is an alkylcarbonyl group having greater than 14 carbons and less than 30 carbons, and $R^3$ is 2,3-dihydroxypropyl, or a physiologically acceptable salt thereof, wherein the concentration of the lysophosphatidyl glycerol in the solution is at least 0.05%.

2. The drug delivery system according to claim 1 wherein the alkylcarbonyl group contains greater than 14 carbon atoms and less than 19 carbon atoms.

3. A drug delivery system comprising a pharmacologically active compound and an absorption enhancer in the form of biocompatible polymeric microspheres having a diameter of less than 100 microns formulated for administration to mucosal surfaces, wherein the absorption enhancer is a lysophosphatidyl glycerol of the general formula I

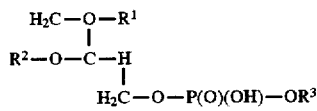

wherein one of $R^1$ and $R^2$ is hydrogen and the other is an alkylcarbonyl group having greater than 14 carbons and less than 30 carbons, and $R^3$ is 2,3-dihydroxypropyl, or a physiologically acceptable salt thereof.

4. The drug delivery system according to claim 3 wherein the microspheres comprise a polymeric material selected from the group consisting of starches, gelatin, albumin, collagen, and dextrans.

5. The drug delivery system according to claim 1 formulated for administration to nasal mucosal surfaces.

6. The drug delivery system of claim 1 or 3 wherein the pharmacologically active compound is selected from the group consisting of insulin and calcitonin.

7. A process for preparing a drug delivery system comprising admixing a pharmacologically active compound and an absorption enhancer formulated into a solution having a concentration of at least 0.05% concentration enhancer or microspheres for administration to mucosal surfaces, wherein the absorption enhancer is a lysophosphatidyl glycerol of the general formula I

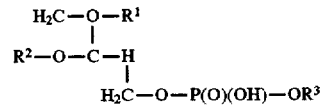

wherein one of $R^1$ and $R^2$ is hydrogen and the other is an alkylcarbonyl group having greater than 14 carbons and less than 30 carbons, and $R^3$ is 2,3-dihydroxypropyl, or a physiologically acceptable salt thereof.

8. A method of treating a vertebrate comprising administering to mucosal surfaces of said vertebrate a drug delivery system comprising a pharmacologically active compound and an absorption enhancer formulated into a solution having a concentration of at least 0.05% concentration enhancer or microspheres for administration to mucosal surfaces, wherein the absorption enhancer is a lysophosphatidyl glycerol of the general formula I

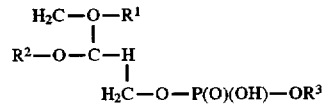

wherein one of $R^1$ and $R^2$ is hydrogen and the other is an alkylcarbonyl group having greater than 14 carbons and less than 30 carbons, and $R^3$ is 2,3-dihydroxypropyl, or a physiologically acceptable salt thereof.

9. The method of claim 8 for treating a diabetic human being comprising administering to mucosal surfaces of the human being the drug delivery system wherein the pharmacologically active compound is insulin.

10. The drug delivery system of claim 1 or 3 comprising:

a pharmacologically active substance selected from the group consisting of insulin, calcitonin and synthetic modifications thereof, growth hormones, glucagon, interferons, secretin, bradykinin antagonists, growth hormone releasing factor, thyrotropin releasing hormone, ACTH analogues, insulin-like growth factors, enkephalins, LHRH and analogues, growth hormone releasing hormone, nifedipin, thymic humoral factor, calcitonin gene related peptide, atrial natriuretic peptide, metoclopramide, ergotamine, dihydroergotamine, ergometrine, Pizotizin, nasal vaccines, Factor VIII, pentamidine, cholecystokinin (CCK), desmopressin and DDAVP analogues, vasopressin, antimicrobial agents, anesthetics, vasoconstrictors, cardiotonics, vasodilators, enzymes, bone metabolism controlling agents, sex hormones, hypotensives, sedatives, anti-tumor agents, anti-allergic agents, antitussive-expectorant agents, and antiasthmatic agents; and a physiological acceptable diluent

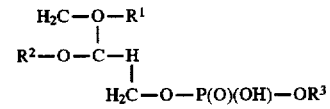

which drug delivery system, when administered to a mucosal surface enhances the systemic uptake of the pharmacologically active agent without damaging the surface epithelium of the mucosa at the site of administration.

* * * * *

UNITED STATES PATENT AND TRADEMARK OFFICE
CERTIFICATE OF CORRECTION

PATENT NO. : 5,725,871
DATED : March 10, 1998
INVENTOR(S) : Lisbeth Illum

It is certified that error appears in the above-identified patent and that said Letters Patent is hereby corrected as shown below:

Column 2,
Lines 38-41, delete the formula and replace it with the following:

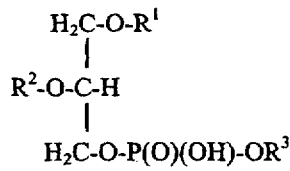

Column 10, claim 1,
Line 42, cancel beginning with "1. A drug delivery system" to and including "0.05%"

Column 10,
Line 58, and insert the following claim:
1. A drug delivery system comprising a pharmacologically active compound and an absorption enhancer formulated for administration to mucosal surfaces, wherein the absorption enhancer is a lysophosphatidyl glycerol of the general formula I

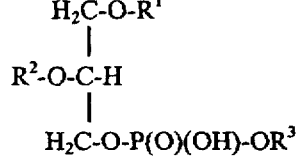

wherein one of $R^1$ and $R^2$ is hydrogen and the other [includes greater than 14 carbons and less than 30 carbons and is selected from the group consisting alkyl, alkenyl, alkylcarbonyl, alkenylcarbonyl, alkadienylcarbonyl, alkatrienylcarbonyl and alkatetraenylcarbonyl, and $R^3$ is 2,3-dihydroxypropyl, or a physiologically acceptable salt thereof, wherein the concentration of the lysophosphatidyl glycerol in the formulation] is at least 0.05%. --

Column 10, claim 3,
Line 62, cancel beginning with "3. A drug delivery system" to and including "acceptable salt thereof" in column 11, line 10, and insert the following claim:
-- 3. A drug delivery system comprising [microspheres, wherein the microspheres comprise a pharmacologically active compound and an absorption enhancer, wherein the microspheres have a diameter of less than 100 microns, and wherein the drug delivery system is formulated for administration to mucosal surfaces,

UNITED STATES PATENT AND TRADEMARK OFFICE
CERTIFICATE OF CORRECTION

PATENT NO. : 5,725,871  
DATED : March 10, 1998  
INVENTOR(S) : Lisbeth Illum

Page 2 of 4

It is certified that error appears in the above-identified patent and that said Letters Patent is hereby corrected as shown below:

wherein the absorption enhancer is a lysophosphatidyl glycerol of the general formula I

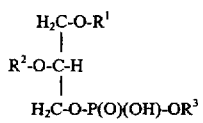

wherein one of $R^1$ and $R^2$ is hydrogen and the other includes greater than 14 carbons and less than 30 carbons and is selected from the group consisting of alkyl, alkenyl, alkylcarbonyl, alkenylcarbonyl, alkadienylcarbonyl, alkatrienylcarbonyl and alkatetraenylcarbonyl,] and $R^3$ is 2,3-dihydroxypropyl, or a physiologically acceptable salt thereof. --

Column 11, claim 4,  
Line 11, cancel beginning with "4. The drug delivery system" to and including "collagen, and dextrans" in column 11, line 15, and insert the following claim:  
-- 4. The drug delivery system according to claim 3 wherein the [polymeric microspheres are formed of a polymeric material selected from the group consisting of starches, gelatin, albumin, collagen, and dextrans, and wherein the microspheres comprise the pharmacologically active compound. --]

Column 11, claim 7,  
Line 21, cancel beginning with "7. A process for preparing" to and including "acceptable salt thereof" in col. 11, line 39, and insert the following:  
-- 7. A process for preparing a drug delivery system comprising admixing a pharmacologically active compound and an absorption enhancer [in the form of a formulation having a concentration of at least 0.05% enhancer or in the form of microspheres for administration to mucosal surfaces, wherein the absorption enhancer is a lysophosphatidyl glycerol of the general formula I

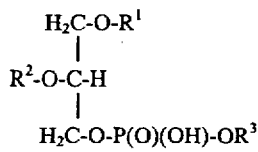

wherein one of $R^1$ and $R^2$ is hydrogen and the other includes greater than 14 carbons and less than 30 carbons and is selected from the group consisting of alkyl, alkenyl, alkylcarbonyl, alkenylcarbonyl, alkadienylcarbonyl, alkatrienylcarbonyl and alkatetraenylcarbonyl,] and $R^3$ is 2,3-dihydroxypropyl, or a physiologically acceptable salt thereof. --

UNITED STATES PATENT AND TRADEMARK OFFICE
CERTIFICATE OF CORRECTION

PATENT NO. : 5,725,871
DATED : March 10, 1998
INVENTOR(S) : Lisbeth Illum

It is certified that error appears in the above-identified patent and that said Letters Patent is hereby corrected as shown below:

Column 11, claim 8,
Line 40, cancel beginning with "8. A method of treating" to and including "acceptable salt thereof" in column 12, line 10, and insert the following claim:
-- 8. A method of treating a vertebrate comprising administering to mucosal surfaces of said vertebrate a drug delivery system comprising a pharmacologically active compound and an absorption enhancer [in the form of a formulation having a concentration of at least 0.05% enhancer or in the form of microspheres for administration to mucosal surfaces, wherein the absorption enhancer is a lysophosphatidyl glycerol of the general formula I

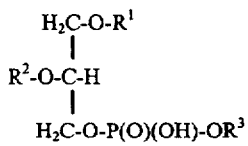

wherein one of $R^1$ and $R^2$ is hydrogen and the other includes greater than 14 carbons and less than 30 carbons and is selected from the group consisting of alkyl, alkenyl, alkylcarbonyl, alkenylcarbonyl, alkadienylcarbonyl, alkatrienylcarbonyl and alkatetraenylcarbonyl,] and $R^3$ is 2,3-dihydroxypropyl, or a physiologically acceptable salt thereof. --

Column 12, claim 10,
Line 17, delete "and synthetic";
Line 18, delete "modifications thereof";
Line 28, delete "desmopressin and DDAVP analogues" and insert-- desmopressins -- in place thereof,
Line 31, delete "bone metabolism controlling agents" and insert -- Vitamins [D and $D_{3S}$] in place thereof;
Lines 38-41, delete the formula;
Line 43, delete "which" and insert -- wherein the -- in place thereof.

UNITED STATES PATENT AND TRADEMARK OFFICE
CERTIFICATE OF CORRECTION

PATENT NO. : 5,725,871
DATED : March 10, 1998
INVENTOR(S) : Lisbeth Illum

It is certified that error appears in the above-identified patent and that said Letters Patent is hereby corrected as shown below:

Column 12,
Line 47, insert the claims:
-- 11. The drug delivery system of claim 3 wherein the pharmacologically active compound is selected from the group consisting of a peptide and a protein, and wherein the microspheres are formed of the pharmacologically active compound. --
-- 12. The drug delivery system of claim 11 wherein the pharmacologically active compound is insulin. --
-- 13. The drug delivery system of claim 3 wherein the microspheres are capable of controlled release of the pharmacologically active agent. --
-- 14. The drug delivery system of claim 1 wherein the formulation is a solution. --
-- 15. The drug delivery system of claim 1 wherein the formulation is a powder. --
-- 16. The process of claim 7 wherein the formulation is a solution. --
-- 17. The process of claim 7 wherein the formulation is a powder. --
-- 18. The method of claim 8 wherein the formulation is a solution. --
-- 19. The method of claim 8 wherein the formulation is a powder. --

Signed and Sealed this

Eighth Day of January, 2002

Attest:

Attesting Officer

JAMES E. ROGAN
Director of the United States Patent and Trademark Office